(12) United States Patent
Pretz et al.

(10) Patent No.: US 11,059,763 B2
(45) Date of Patent: Jul. 13, 2021

(54) METHODS AND APPARATUSES FOR PROCESSING GAS STREAMS

(71) Applicant: Dow Global Technologies LLC, Midland, MI (US)

(72) Inventors: Matthew T. Pretz, Freeport, TX (US); Madhusudhan Kodam, Indianapolis, IN (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/634,335

(22) PCT Filed: Jul. 30, 2018

(86) PCT No.: PCT/US2018/044310
§ 371 (c)(1),
(2) Date: Jan. 27, 2020

(87) PCT Pub. No.: WO2019/027870
PCT Pub. Date: Feb. 7, 2019

(65) Prior Publication Data
US 2020/0231521 A1 Jul. 23, 2020

Related U.S. Application Data

(60) Provisional application No. 62/538,987, filed on Jul. 31, 2017.

(51) Int. Cl.
*C07C 5/333* (2006.01)
*B01J 8/18* (2006.01)
*B01J 8/26* (2006.01)

(52) U.S. Cl.
CPC .............. *C07C 5/333* (2013.01); *B01J 8/1827* (2013.01); *B01J 8/1854* (2013.01); *B01J 8/1872* (2013.01); *B01J 8/26* (2013.01)

(58) Field of Classification Search
None
See application file for complete search history.

(56) References Cited

U.S. PATENT DOCUMENTS

| | | | |
|---|---|---|---|
| 3,123,547 A | 3/1964 | Palmer et al. | |
| 3,308,196 A * | 3/1967 | Bajars | C07C 5/56 585/618 |
| 3,767,566 A | 10/1973 | Cartmell | |

(Continued)

FOREIGN PATENT DOCUMENTS

EP 0063901 A1 11/1982

OTHER PUBLICATIONS

Wang et al., "Comparison study for the oxidative dehydrogenation of isopentenes to isoprene in fixed and fluidized beds", Catalysis Today 276, 2016, p. 78-84. (Year: 2016).*

(Continued)

*Primary Examiner* — Philip Y Louie
(74) *Attorney, Agent, or Firm* — Dinsmore & Shohl LLP

(57) ABSTRACT

According to one or more embodiments disclosed herein, a reactant gas may be converted by a method comprising introducing the reactant gas to a fluidized bed reactor. The main reactor vessel of the fluidized bed reactor may be tapered such that the upstream portion of the main reactor vessel comprises a lesser cross-sectional area than the downstream portion of the main reactor vessel.

14 Claims, 3 Drawing Sheets

(56) References Cited

U.S. PATENT DOCUMENTS

| | | |
|---|---|---|
| 4,579,716 A | 4/1986 | Krambeck et al. |
| 5,037,616 A | 8/1991 | Williatte et al. |
| 5,190,650 A | 3/1993 | Tammera et al. |
| 5,275,641 A | 1/1994 | Tammera et al. |
| 6,166,282 A | 12/2000 | Miller |
| 7,101,474 B2 | 9/2006 | Sattar |
| 7,169,293 B2 | 1/2007 | Lomas et al. |
| 7,396,971 B2 | 7/2008 | Smith et al. |
| 7,575,725 B2 | 8/2009 | Lomas et al. |
| 7,902,416 B2 | 3/2011 | Glover et al. |
| 2007/0213573 A1 | 9/2007 | Ross et al. |

OTHER PUBLICATIONS

Chalermsinsuwan et al., "CFD modeling of tapered circulating fluidized bed reactor risers: Hydrodynamic descriptions and chemical reaction responses", Chemical Engineering and Processing, 49, 2010, p. 1144-1160. (Year: 2010).*

International Search Report and Written Opinion pertaining to PCT/US2018/044310, dated Oct. 9, 2018.

Kunii et al., "Entrainment of solids from fluidized beds", Powder Technology, 61, 1990, 193-206.

* cited by examiner

METHODS AND APPARATUSES FOR PROCESSING GAS STREAMS

CROSS REFERENCE TO RELATED APPLICATION

This application claims priority to U.S. Provisional Patent Application Ser. No. 62/538,987 filed Jul. 31, 2017, which is incorporated by reference herein in its entirety.

BACKGROUND

Field

The present disclosure generally relates to chemical processing, and more specifically, to reactor designs and systems utilized in chemical processing.

Technical Background

Many reactions utilizing gas streams as reactants form additional moles of gas as a result of the reaction (i.e., when more molecules of gas exist after reaction than before). For example, dehydrogenation and cracking reactions produce additional moles of product compared to that which existed in the reactant stream. When the reactant and product are gases, changes in local gas velocities may result in the reactor by the formation of these additional molecules.

BRIEF SUMMARY

Where a reaction produces additional gas molecules as compared with that of the reactant stream, pressure may build in the reactor or other system components. These changes in pressure may result in local changes in gas and/or solid catalyst velocity in a reactor, such as a fluidized bed reactor. Changes in gas velocity may also affect the suspension density in a local portion of the reactor, which correlates generally to the amount of catalyst per volume in the reactor at a local position. Controlling fluid superficial velocity and/or suspension density in a reactor may be important to overall chemical conversion rate of a reaction and/or operational specifications (e.g., size, shape, etc.) of a reactor. Accordingly, there is a continued need for methods and apparatuses for processing gas streams under reaction conditions which increase the number of molecules of gas while controlling superficial velocity and/or suspension density throughout the reactor.

More specifically, it has been found that the formation of excess gas molecules following reaction with respect to the amount of gas of the feed reactant may cause increases in the gas superficial velocity and decreases to the suspension density of contents of the reactor. As used herein, "suspension density" refers to the density calculated from both solids contents (e.g., catalyst) and gas contents (e.g., gaseous reactants and products) in the reactor. For example, as more gas is produced through reaction, the superficial velocity of gases may increase, sometimes drastically, in a fluidized bed reactor. Additionally the suspension density (including the reactant and product gas and solid particulate catalyst) may decrease such that conversion is decreased due to lack of catalyst with respect to reactant gas. Since conversion is negatively affected, reactor volume may need to be increased, adding undesirable capital costs. Additionally, high gas velocity in the reactor can make it difficult to control the amount of catalyst in the system at a given time.

In order to mitigate or entirely stop the rise in gas velocity and the decrease in suspension density, it has been discovered that a fluidized bed reactor with an increasing cross-sectional area may be utilized for gas-based reactions which produce excess gas molecules. For example, a fluidized bed reactor which is more narrow in its upstream portion than its downstream portion may allow for relatively constant gas superficial velocity, suspension density, or both, in the upstream and downstream portions of the fluidized bed reactor. By contrast, conventional fluidized bed reactors with tubular shapes generally have increased gas velocity as a function of height. Proper design of the geometry to the fluidized bed reactor, such as a tapered geometry, can allow for reduced increases in gas velocity and/or losses in suspension density as the reaction progresses in downstream portions of the reactor. That is, as the reaction occurs along the height of the reactor (assuming reaction products are moving upwardly), the increase in cross-sectional area compensates for the increase in gas volume and therefore may maintain relatively constant gas velocity. The relative stability of the gas velocity, the suspension density, or both, may allow for mitigation of the problems discussed hereinabove.

According to one or more embodiments, a reactant gas may be converted by a method comprising introducing the reactant gas to a fluidized bed reactor such that the reactant gas is contacted by a catalyst, catalytically reacting the reactant gas to form a reaction product in the fluidized bed reactor, and passing the reaction product and any unreacted reactant gas through a transition section. The fluidized bed reactor may comprise a main reactor vessel comprising an upstream portion and a downstream portion, and a transition section connected to the downstream portion of the main reactor vessel. The reactant gas may enter the fluidized bed reactor at or near the upstream portion of the main reactor vessel. The reaction may result in additional gas molecules relative to the reactant gas. The main reactor vessel may be tapered such that the upstream portion of the main reactor vessel comprises a lesser cross-section area than the downstream portion of the main reactor vessel such that the superficial velocity of the gases in the fluidized bed reactor at the downstream portion of the main reactor vessel may be less than or equal to 140% of the superficial velocity of the gases in the fluidized bed reactor at the upstream portion of the main reactor vessel. According to one or more additional embodiments, a reactant gas may be converted by a method comprising introducing the reactant gas to a fluidized bed reactor such that the reactant gas is contacted by a catalyst, catalytically reacting the reactant gas to form a reaction product in the fluidized bed reactor, and passing the reaction product and any unreacted reactant gas through the transition section. The fluidized bed reactor may comprise a main reactor vessel comprising an upstream portion and a downstream portion, and a transition section connected to the downstream portion of the main reactor vessel. The reactant gas may enter the fluidized bed reactor at or near the upstream portion of the main reactor vessel. The reaction may result in additional gas molecules relative to the reactant gas. The main reactor vessel may be tapered such that the upstream portion of the main reactor vessel comprises a lesser cross-section area than the downstream portion of the main reactor vessel such that the suspension density in the fluidized bed reactor at the downstream portion of the main reactor vessel may be greater than or equal to 25% of the suspension density in the fluidized bed reactor at the upstream portion of the main reactor vessel.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
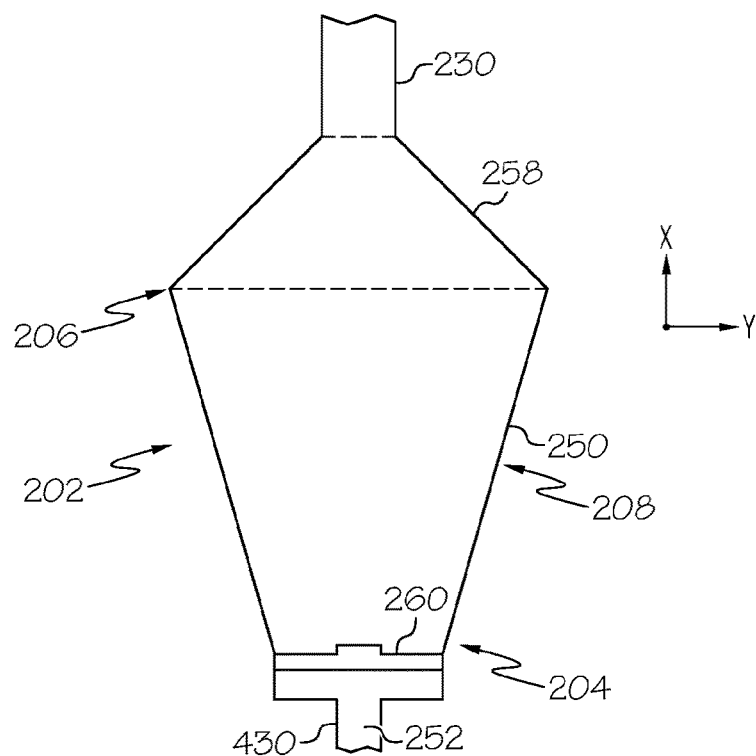
FIG. 1 schematically depicts a fluidized bed reactor, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments related to methods for processing chemical streams in fluidized bed reactor are described herein. In one or more embodiments, the chemical stream that is processed may be referred to as a feed stream or reactant stream, and the chemical stream which includes the product of the chemical reaction may be referred to as a product stream. It should be understood that the product stream may include various components of the feed stream when conversion of the feed stream is incomplete, which may be typical of many chemical reactions.

The systems and apparatuses described herein, such as the fluidized bed reactors described herein, may be utilized as processing equipment for various fluidized catalytic reactions. The methods and apparatuses described may be utilized in reactions wherein a gaseous feed is converted to a gaseous product stream by contact with a solid state catalyst, such as a particulate catalyst. For example, hydrocarbons, as well as other chemical feedstocks, can be converted into desirable products through use of fluidized bed reactors. Fluidized bed reactors serve many purposes in industry, including dehydrogenation of paraffins and/or alkyl aromatics, cracking of hydrocarbons (i.e., fluid catalytic cracking), chlorination of olefins, oxidations of naphthalene to phthalic anhydride, production of acrylonitrile from propylene, ammonia, and oxygen, Fischer-Tropsch synthesis, polymerization of ethylene, dehydration of hydrocarbons to form light olefins, and some methanol to olefin (MTO) reactions.

According to one or more embodiments, some of these reactions, such as without limitation, dehydrogenation, cracking, dehydration, and MTO, may form additional moles of gas molecules with respect to the moles of feed gas molecules. When the products are gaseous, the local pressure in the reactor may be increased as the reaction progresses. Such reactions, in some embodiments, may be represented by the formula aR 4→bP+cZ, where R represented the reactant species, P represented the product species, Z represents another product species, and a, b, and c each represent the relative amount of each species utilized in the reaction. For example, a dehydrogenation reaction would result in hydrogen as Z, or in a dehydration reaction Z would be water. When a is less than b+c, additional molecules are formed by the reaction, which are the reactions for which the presently described methods are apparatuses may be directed. As such, these reaction forms two or more product molecules from each reactant molecule which is reacted. It is noted that the above equation is only one example chemical reaction, and it should be understood that other reactions are within the scope of this disclosure, such as those where two or more products and/or reactants are present.

According to some embodiments, the fluidized bed reactors described herein may process reactant gas comprising ethane, propane, n-butane, isobutane, and ethylbenzene (for example, at least 80 wt. %, 90 wt. %, 95 wt. %, or even 99 wt. % of any of these reactant gases, or combinations thereof) to form product gas comprising ethene, propene, butene isomers and butadiene, isobutene, styrene, or combinations thereof (for example, at least at least 10 wt %, at least 20 wt. %, at least 30 wt. %, at least 40 wt. %, at least 50 wt. %, at least 70 wt. % or even at least 90 wt. % of any of these product gases, or combinations thereof). For example, gases suitable for dehydrogenation are contemplated herein.

Now referring to FIG. 1, an embodiment of a fluidized bed reactor is depicted, which may process a feed stream by contact with a solid catalyst. According to one or more embodiments described herein, the fluidized bed reactor 202 may comprise a main reactor vessel 250, a transition section 258, and a downstream reactor section 230, such as a riser. The transition section 258 may connect the main reactor vessel 250 with the downstream reactor section 230. As depicted in FIG. 1, the main reactor vessel 250 may be positioned below the downstream reactor section 230. Such a configuration may be referred to as an upflow configuration in the fluidized bed reactor 202. A transport riser 430 may supply one or more of reactant gas and catalyst to the fluidized bed reactor 202, and the gaseous reactants and products, as well as the catalyst, may move through a feed distributor 260, through the main reactor vessel 250, through the transition section 258, and into and through the downstream reactor section 230. As depicted in FIG. 1, the movement of the catalyst and product and reactant gases is upward (depicted by the x-axis). As described herein, "superficial velocity" refers to the superficial velocity of a material in the direction of overall material flow (through the plane perpendicular to the x-axis).

As described herein, the main reactor vessel 250 may include a vessel, drum, barrel, vat, or other container suitable for a given chemical reaction. In one or more embodiments, the main reactor vessel 250 may have a substantially circular cross-sectional shape (which is representative of the cross-sectional view of FIG. 1). Alternatively, the main reactor vessel 250 may be non-circular in cross-section. For example, the main reactor vessel 250 may comprise cross-sectional shapes of triangles, rectangles, pentagons, hexagons, octagons, ovals, or other polygons or curved closed shapes, or combinations thereof. The main reactor vessel 250, as used throughout this disclosure, may generally include a metallic frame, and may additionally include refractory linings or other materials utilized to protect the metallic frame and/or control process conditions. As depicted in FIG. 1, the main reactor vessel 250 may include a lower reactor portion catalyst inlet port 252 defining the connection of transport riser 430 to the main reactor vessel 250.

The main reactor vessel 250 may be connected to a transport riser 430 which, in operation, may provide processed catalyst and/or reactant chemicals in a feed stream. The processed catalyst and/or reactant chemicals may be mixed with a feed distributor 260 housed in the main reactor vessel 250. In one or more embodiments, the feed distributor 260 may be operable to dispense the first feed stream and the second feed stream at all shroud distributor velocities from 250 ft/s to 80 ft/s. In such embodiments, various feed streams may be utilized while maintaining the desired reactor characteristics, such as operating as a fast fluidized, turbulent, or bubbling bed reactor in the main reactor vessel 250 and as a dilute phase riser reactor in the downstream reactor section 230. For example, according to one or more embodiments, a shroud distributor velocity of about 80 ft/s may be utilized in the main reactor vessel 250 for naphtha feeds, while a shroud distributor velocity of about 250 ft/s may be utilized in the main reactor vessel 250 for propane feeds. In additional embodiments, some orifices could be closed in the fluidized bed reactor 202 when naphtha is utilized as a feed stream. The "shroud distributor velocity" refers the velocity at which the gas exits the distributor, sometimes through a shroud. For example, suitable distributors are disclosed in U.S. Pat. No. 9,370,759, the teachings of which are incorporated herein by reference in their entirety.

As depicted in FIG. 1, the main reactor vessel 250 may be connected to the downstream reactor section 230 via the transition section 258. The transition section 258 may be tapered from the size of the cross-section of the main reactor vessel 250 to the size of the cross-section of the downstream reactor section 230 such that the transition section 258 projects inwardly from the main reactor vessel 250 to the downstream reactor section 230.

In one or more embodiments, the downstream reactor section 230 may be generally cylindrical in shape (i.e., having a substantially circular cross-sectional shape), or may alternately be non-cylindrically shaped, such as prism shaped with cross-sectional shape of triangles, rectangles, pentagons, hexagons, octagons, ovals, or other polygons or curved closed shapes, or combinations thereof. The downstream reactor section 230, as used throughout this disclosure, may generally include a metallic frame, and may additionally include refractory linings or other materials utilized to protect the metallic frame and/or control process conditions.

In some embodiments, such as those where the main reactor vessel 250 and the downstream reactor section 230 have similar cross-sectional shapes, the transition section 258 may be shaped as a frustum. For example, for an embodiment of a reactor portion 200 comprising a circular cross-sectioned main reactor vessel 250 and cylindrical downstream reactor section 230, the transition section 258 may be shaped as a conical frustum. However, it should be understood that a wide variety of main reactor vessel 250 shapes are contemplated herein which connect various shapes and sizes of transition sections 258 and downstream reactor sections 230.

According to one or more embodiments, the main reactor vessel 250 may be tapered outwardly with respect to the direction of general flow of materials (i.e., the direction of the x-axis) in the fluidized bed reactor 202. For example, FIG. 1 depicts a linearly expanding main reactor vessel 250, which has the shape of a segment of a cone. While the tapered geometry may be linear in some embodiments, some embodiments disclosed herein are not linearly tapered, such as that depicted in FIG. 2.

Figure 2:
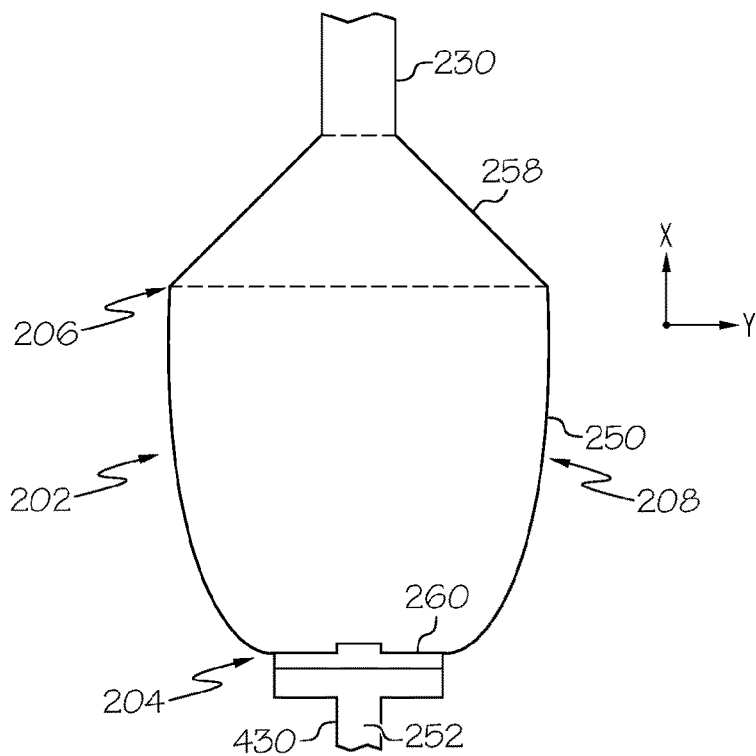
FIG. 2 schematically depicts another fluidized bed reactor, according to one or more embodiments described herein.

Referring to FIG. 1 or 2, the main reactor vessel 250 may comprise an upstream portion 204 and a downstream portion 206. The upstream portion 204 may be the portion of the main reactor vessel 250 adjacent the feed distributor 260 and the downstream portion 206 may be the portion of the main reactor vessel 250 adjacent the transition section 258. A central portion 208 of the main reactor vessel 250 may be positioned equidistant between the upstream portion 204 and the downstream portion 206 (based on the height in the x-direction of the main reactor vessel 250). Generally, the upstream portion 204 of the main reactor vessel 250 may have a lesser cross-sectional area than the downstream portion 206 of the main reactor vessel 250, defining a taper in the cross-sectional geometry of the main reactor vessel 250. As described herein, unless otherwise explicitly stated, the "cross-sectional area" refers to the area of the cross section of a portion of the reactor part in a plane substantially orthogonal to the direction of average flow of reactants and/or products (i.e., the plane perpendicular to the x-axis in FIG. 1). For example, in FIG. 1, the cross sectional area of the main reactor vessel 250, the transition section 258, and the downstream reactor section 230, or any portion of each, is in the direction of a plane defined by the horizontal direction and the direction into the page (orthogonal to the direction of fluid motion, i.e., vertically upward in FIG. 1). In additional embodiments, the upstream portion 204 may have a lesser cross-sectional area than the central portion 208, and the central portion 208 may have a lesser cross-sectional area than the downstream portion 206. As such, in some embodiments, the cross-sectional area of the central portion 208 may be less than the cross-sectional area of the downstream portion 206 and greater than the cross-sectional area of the upstream portion 204.

In one or more embodiments, the cross-sectional area of the downstream portion 206 of the main reactor vessel 250 may be from 1.2 to 1.8 times that of the upstream portion 204 of the main reactor vessel 250 (e.g., from 1.2 to 1.4, from 1.4 to 1.6, or from 1.6 to 1.8). According to one or more embodiments, the main reactor vessel 250 may have a height of from 2 ft to 12 ft (e.g., from 2 ft to 4 ft, from 4 ft to 6 ft, from 6 ft to 8 ft, from 8 ft to 10 ft, or from 10 ft to 12 ft).

In one or more embodiments, the taper of the main reactor vessel 250 may be described by a slope at a particular portion of the main reactor vessel 250. For example, the main reactor vessel 250 may have a measurable slope (i.e., half the width change divided by the height change) at the upstream portion 204, the downstream portion 206, and the central portion 208. That is, a constant cross-sectional shape would have a slope of 0. In the embodiment of FIG. 1, the slope may be substantially constant across the main reactor vessel 250, such as substantially constant with respect to the upstream portion 204, the downstream portion 206, and the central portion 208. Such a substantially constant slope corresponds to a linear profile of the main reactor vessel 250. In additional embodiments, such as that of FIG. 2, the main reactor vessel 250 may comprise a slope that is less at or near the downstream portion 206 than at or near the upstream portion 204 of the main reactor vessel 250. In such embodiments, the slope at the central portion 208 may be less than that of the upstream portion 204 and greater than that of the downstream portion 206. As is explained in the Examples which follow, the slope and relative shape of the main reactor vessel 250 may affect the superficial gas velocity and/or the suspension density at local positioned within the main reactor vessel 250.

As depicted in FIGS. 1 and 2, the inwardly tapered transition section 258 and outwardly tapered main reactor vessel 250 form a geometric configuration of the fluidized bed reactor 202 in which the portion of the fluidized bed reactor 202 with the largest cross-sectional area is at the point where the transition section 258 and main reactor vessel 250 are connected (i.e., at or near the downstream portion 206 of the main reactor vessel 250). The downstream reactor section 230 may have a lesser cross-sectional area than the transition section 258 and the main reactor vessel 250. In one or more embodiments, the downstream reactor section 230 may have a smaller cross-sectional area than the upstream portion 204 of the main reactor vessel 250.

According to the embodiments described herein, at least one purpose of the outwardly tapered main reactor vessel 250 is its effect upon the gas superficial velocity and/or suspension density at local positions in the main reactor vessel 250. It may be desirable to have relatively constant gas superficial velocity and/or suspension density along the height of the main reactor vessel 250. For example, it may be desirable to have similar gas superficial velocity and/or suspension density at two or more of the upstream portion 204 as at the downstream portion 206 or central portion 208.

According to one more embodiments, the superficial velocity of the gases in the fluidized bed reactor at the downstream portion 206 of the main reactor vessel 250 may be less than or equal to 140% (such as, e.g., less than or equal to 130%, less than or equal to 120%, less than or equal to 110%, less than or equal to 100%, less than or equal to 90%, or even less than or equal to 80%) of the superficial velocity of the gases in the fluidized bed reactor at the upstream portion 204 of the main reactor vessel 250. For example, in additional embodiments, the superficial velocity of the gases in the fluidized bed reactor at the downstream portion 206 of the main reactor vessel may be from 60% to 140%, from 70% to 130%, from 80% to 120%, or even from 90% to 110% of the superficial velocity of the gases in the fluidized bed reactor at the upstream portion 204 of the main reactor vessel. In additional embodiments, the superficial velocity of the gases in the fluidized bed reactor at the downstream portion 206 of the main reactor vessel 250, at the upstream portion 204 of the main reactor vessel 250, or both, may be less than or equal to 140% (such as, e.g., less than or equal to 130%, less than or equal to 120%, less than or equal to 110%, less than or equal to 100%, less than or equal to 90%, or even less than or equal to 80%) of the superficial velocity of the gases in the fluidized bed reactor at the central portion 208 of the main reactor vessel 250. For example, the superficial velocity of the gases in the fluidized bed reactor at the downstream portion 206 of the main reactor vessel 250, at the upstream portion 204 of the main reactor vessel 250, or both, may be from 60% to 140%, from 70% to 130%, from 80% to 120%, or even from 90% to 110% of the superficial velocity of the gases in the fluidized bed reactor at the central portion 208 of the main reactor vessel 250.

According to additional embodiments, the suspension density in the fluidized bed reactor at the downstream portion 206 of the main reactor vessel 250 may greater than or equal to 25% (such as greater than or equal to 35%, greater than or equal to 50%, or even greater than or equal to be from 75%) of the suspension density in the fluidized bed reactor at the upstream portion 204 of the main reactor vessel 250. For example, in additional embodiments, the suspension density in the fluidized bed reactor at the downstream portion 206 of the main reactor vessel 250 may be from 25% to 175%, from 50% to 150%, from 80% to 120%, or even from 90% to 110% of the suspension density in the fluidized bed reactor at the upstream portion 204 of the main reactor vessel. In additional embodiments, the suspension density in the fluidized bed reactor at the central portion 208 of the main reactor vessel 250 may be from greater than or equal to 40%, 50%, 60%, 70%, or even 80% of the suspension density in the fluidized bed reactor at the upstream portion 204 of the main reactor vessel 250.

As described herein, the superficial velocity at the upstream portion 204 and the downstream portion 206 of the main reactor vessel 250 may be determined by utilizing known equations such as the ideal gas law with measurable properties of the streams within the fluidized bed reactor 202. The temperature and pressure at the upstream portion 204 and the downstream portion 206 of the main reactor vessel 250, respectively, as well as the mass flowrates and gas compositions entering and exiting the main reactor vessel 250 may be utilized to determine the superficial velocity at the upstream portion 204 and the downstream portion 206 of the main reactor vessel 250. For example, temperature and pressure probes may be used within the fluidized bed reactor and slip streams at heights along the fluidized bed reactor can be determinative of the gas composition as a particular height. Additionally, the suspension density may be determined by comparing the pressure at two reactor heights and applying known equations. It should be understood that since two measurements may be required to determine the suspension density, the suspension density at the upstream portion 204 may be measured by data collected from the area adjacent the distributor and one foot downstream of (e.g., above) the distributor. Similarly, the suspension density at the downstream portion 206 may be measured by data collected from the area adjacent the transition section 258 and one foot upstream of (e.g., below) the transition section 258.

In one or more embodiments, based on the shape, size, and other processing conditions such as temperature and pressure in the main reactor vessel 250 and the downstream reactor section 230, the main reactor vessel 250 may operate in a manner that is or approaches isothermal, such as in a fast fluidized, turbulent, or bubbling bed reactor, while the downstream reactor section 230 may operate in more of a plug flow manner, such as in a dilute phase riser reactor. For example, the fluidized bed reactor 202 of FIG. 1 may comprise a main reactor vessel 250 operating as a fast fluidized, turbulent, or bubbling bed reactor and a downstream reactor section 230 operating as a dilute phase riser reactor, with the result that the average catalyst and gas flow moves concurrently upward. As the term is used herein, "average flow" refers to the net flow, i.e., the total upward flow minus the retrograde or reverse flow, as is typical of the behavior of fluidized particles in general. As described herein, a "fast fluidized" reactor may refer to a reactor utilizing a fluidization regime wherein the superficial velocity of the gas phase is greater than the choking velocity and may be semi-dense in operation. As described herein, a "turbulent" reactor may refer to a fluidization regime where the superficial velocity of less than the choking velocity and is more dense than the fast fluidized regime. As described herein, a "bubbling bed" reactor may refer to a fluidization regime wherein well defined bubbles in a highly dense bed are present in two distinct phases. The "choking velocity" refers to the minimum velocity required to maintain solids in the dilute-phase mode in a vertical conveying line. As described herein, a "dilute phase riser" may refer to a riser reactor operating at transport velocity, where the gas and catalyst have about the same velocity in a dilute phase.

In one or more embodiments, the pressure in the fluidized bed reactor 202 may range from 6.0 to 44.7 pounds per square inch absolute (psia, from about 41.4 kilopascals, kPa, to about 308.2 kPa), but in some embodiments, a narrower selected range, such as from 15.0 psia to 35.0 psia, (from about 103.4 kPa to about 241.3 kPa), may be employed. For example, the pressure may be from 15.0 psia to 30.0 psia (from about 103.4 kPa to about 206.8 kPa), from 17.0 psia to 28.0 psia (from about 117.2 kPa to about 193.1 kPa), or from 19.0 psia to 25.0 psia (from about 131.0 kPa to about 172.4 kPa). Unit conversions from standard (non-SI) to metric (SI) expressions herein include "about" to indicate rounding that may be present in the metric (SI) expressions as a result of conversions.

In additional embodiments, the weight hourly space velocity (WHSV) for the disclosed process may range from 0.1 pound (lb) to 100 lb of chemical feed per hour (h) per lb of catalyst in the reactor (lb feed/h/lb catalyst). For example, where a reactor comprises a main reactor vessel 250 that operates as a fast fluidized, turbulent, or bubbling bed reactor and a downstream reactor section 230 that operates as a riser reactor, the superficial gas velocity may range therein from 2 feet per second (ft/s, about 0.61 meters per second, m/s) to 80 ft/s (about 24.38 m/s), such as from 2 ft/s (about 0.61 m/s) to 10 ft/s (about 3.05 m/s), in the main reactor vessel 250, and from 30 ft/s (about 9.14 m/s) to 70 ft/s (about 21.31 m/s) in the downstream reactor section 230. In additional embodiments, a reactor configuration that is fully of a riser type may operate at a single high superficial gas velocity, for example, in some embodiments at least 30 ft/s (about 9.15 m/s) throughout.

In additional embodiments, the ratio of catalyst to feed stream in the fluidized bed reactor 202 may range from 5 to 100 on a weight to weight (w/w) basis. In some embodiments, the ratio may range from 10 to 40, such as from 12 to 36, or from 12 to 24.

In additional embodiments, the catalyst flux may be from 1 pound per square foot-second (lb/ft$^2$-s) (about 4.89 kg/m$^2$-s) to 20 lb/ft$^2$-s (to about 97.7 kg/m2-s) in the main reactor vessel 250, and from 10 lb/ft$^2$-s (about 48.9 kg/m2-s) to 100 lb/ft$^2$-s (about 489 kg/m2-s) in the downstream reactor section 230.

According to additional embodiments, the fluidized bed reactor 202 may include internal structures such as those described in U.S. Pub. No. 2016/0375419, the contents of which are incorporated by reference in their entirety.

Figure 3:
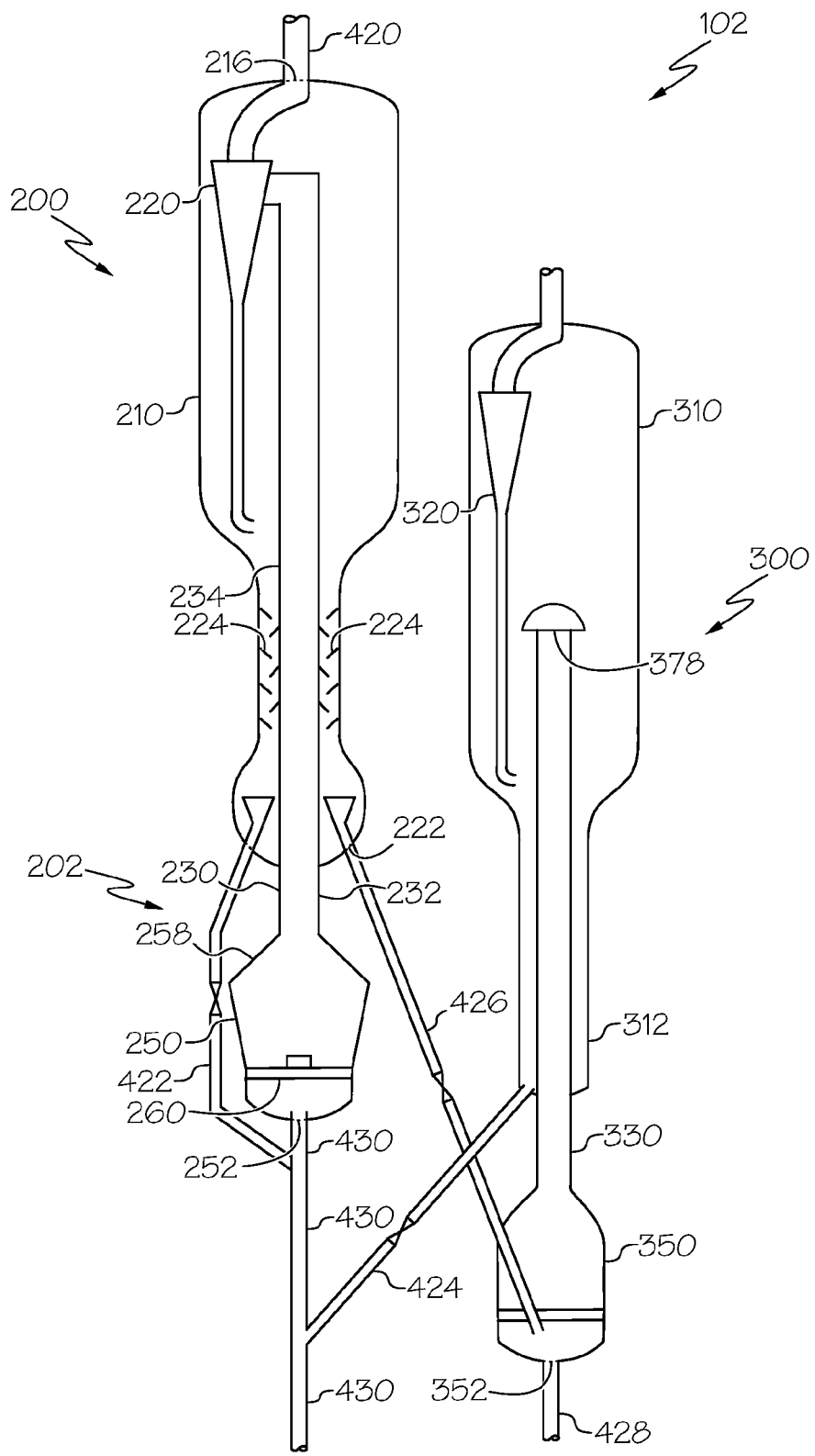
FIG. 3 schematically depicts an example chemical processing system that may utilize the presently described fluidized bed reactors, according to one or more embodiments described herein.

Now referring to FIG. 3, an example reactor system 102 which may incorporate a fluidized bed reactor (such as that of FIG. 1 or FIG. 2) and be suitable for use with the methods described herein is schematically depicted. It should be understood that the system of FIG. 3 is only an example system, and other systems may be utilized with the fluidized bed reactors described herein.

The reactor system 102 generally comprises multiple system components, such as a reactor portion 200 and/or a catalyst processing portion 300. As used herein in the context of FIG. 2, the reactor portion 200 generally refers to the portion of a reactor system 102 in which the major process reaction takes place, such as a dehydrogenation reaction, a cracking reaction, a dehydration reaction, or a methanol-to-olefin reaction to, for example, form light olefins. The reactor portion 200 comprises a fluidized bed reactor 202 which may include a downstream reactor section 230 and a main reactor vessel 250. According to one or more embodiments, as depicted in FIG. 3, the reactor portion 200 may additionally include a catalyst separation section 210 which serves to separate the catalyst from the chemical products formed in the fluidized bed reactor 202. Also, as used herein, the catalyst processing portion 300 generally refers to the portion of a reactor system 102 where the catalyst is in some way processed, such as by combustion. The catalyst processing portion 300 may comprise a combustor 350 and a riser 330, and may optionally comprise a catalyst separation section 310. In some embodiments, the catalyst may be regenerated by burning off contaminants like coke in the catalyst processing portion 300. In additional embodiments, the catalyst may be heated in the catalyst processing portion 300. A supplemental fuel may be utilized to heat the catalyst in the catalyst processing portion 300 if coke or another combustible material is not formed on the catalyst, or an amount of coke formed on the catalyst is not sufficient to burn off to heat the catalyst to a desired temperature. In one or more embodiments, the catalyst separation section 210 may be in fluid communication with the combustor 350 (e.g., via standpipe 426) and the catalyst separation section 310 may be in fluid communication with the main reactor vessel 250 (e.g., via standpipe 424 and transport riser 430).

As depicted with respect to FIG. 3, the feed stream may enter a transport riser 430, and the product stream may exit the reactor system 102 via pipe 420. According to one or more embodiments, the reactor system 102 may be operated by feeding a chemical feed (e.g., in a feed stream) and a fluidized catalyst into the main reactor vessel 250. The chemical feed contacts the catalyst in the main reactor vessel 250, and each flow upwardly into and through the downstream reactor section 230 to produce a chemical product. The chemical product and the catalyst may be passed out of the downstream reactor section 230 to a separation device 220 in the catalyst separation section 210, where the catalyst is separated from the chemical product, which is transported out of the catalyst separation section 210. The separated catalyst is passed from the catalyst separation section 210 to the combustor 350. In the combustor 350, the catalyst may be processed by, for example, combustion. For example, and without limitation, the catalyst may be de-coked and/or supplemental fuel may be combusted to heat the catalyst. The catalyst is then passed out of the combustor 350 and through the riser 330 to a riser termination separator 378, where the gas and solid components from the riser 330 are at least partially separated. The vapor and remaining solids are transported to a secondary separation device 320 in the catalyst separation section 310 where the remaining catalyst is separated from the gases from the catalyst processing (e.g., gases emitted by combustion of spent catalyst or supplemental fuel). The separated catalyst is then passed from the catalyst separation section 310 (via portion 312) to the main reactor vessel 250 via standpipe 424 and transport riser 430, where it is further utilized in a catalytic reaction. Thus, the catalyst, in operation, may cycle between the reactor portion 200 and the catalyst processing portion 300. In general, the processed chemical streams, including the feed streams and product streams may be gaseous, and the catalyst may be fluidized particulate solid.

The catalyst entering the main reactor vessel 250 via transport riser 430 may be passed through standpipe 424 to a transport riser 430, thus arriving from the catalyst processing portion 300. In some embodiments, catalyst may come directly from the catalyst separation section 210 via standpipe 422 and into a transport riser 430, where it enters the main reactor vessel 250. This catalyst may be slightly deactivated, but may still, in some embodiments, be suitable for reaction in the main reactor vessel 250. As used herein, "deactivated" may refer to a catalyst which is contaminated with a substance such as coke, or is cooler in temperature than desired. Regeneration may remove the contaminant such as coke, raise the temperature of the catalyst, or both.

In operation, the catalyst may move upward through the downstream reactor section 230 (from the main reactor vessel 250), and into the separation device 220. In some embodiments, the downstream reactor section 230 may comprise an internal portion 234 (i.e., within the catalyst separation section 210) and an external portion 232. The separated vapors may be removed from the reactor system 102 via a pipe 420 at a gas outlet port 216 of the catalyst separation section 210. According to one or more embodiments, the separation device 220 may be a cyclonic separation system, which may include two or more stages of cyclonic separation. In embodiments where the separation device 220 comprises more than one cyclonic separation stages, the first separation device into which the fluidized stream enters is referred to a primary cyclonic separation device. The fluidized effluent from the primary cyclonic separation device may enter into a secondary cyclonic separation device for further separation. Primary cyclonic separation devices may include, for example, primary cyclones, and systems commercially available under the names VSS (commercially available from UOP), LD2 (commercially available from Stone and Webster), and RS2 (commercially available from Stone and Webster). Primary cyclones are described, for example, in U.S. Pat. Nos. 4,579,716; 5,190,650; and 5,275,641, which are each incorporated by reference in their entirety herein. In some separation systems utilizing primary cyclones as the primary cyclonic separation device, one or more set of additional cyclones, e.g. secondary cyclones and tertiary cyclones, are employed for further separation of the catalyst from the product gas. It should be understood that any primary cyclonic separation device may be used in embodiments of the invention.

According to one or more embodiments, following separation from vapors in the separation device 220, the catalyst may generally move through the stripper 224 to the catalyst outlet port 222 where the catalyst is transferred out of the reactor portion 200 via standpipe 426 and into the catalyst processing portion 300. Optionally, the catalyst may also be transferred directly back into the main reactor vessel 250 via standpipe 422. Alternatively, the catalyst may be premixed with processed catalyst in the transport riser 430.

According to one or more embodiments, operating the chemical process, such as in reactor system 102, may comprise recycling the catalyst utilized in the chemical process by passing the catalyst from the fluidized bed reactor 202 to a regeneration unit (such as the combustor 350 of the embodiment of FIG. 2), processing the respective catalyst in the regeneration unit, and passing the first catalyst from the regeneration unit to the fluidized bed reactor 202.

Referring now to the catalyst processing portion 300, as depicted in FIG. 3, the combustor 350 of the catalyst processing portion 300 may include one or more lower reactor section inlet ports 352 and may be in fluid communication with the riser 330. The combustor 350 may be in fluid communication with the catalyst separation section 210 via standpipe 426, which may supply spent catalyst from the reactor portion 200 to the catalyst processing portion 300 for regeneration. The combustor 350 may include an additional lower reactor section inlet port 352 where air inlet 428 connects to the combustor 350. The air inlet 428 may supply reactive gases which may react with the spent catalyst or a supplemental fuel to at least partially regenerate the catalyst. For example, the catalyst may be coked following the reactions in the main reactor vessel 250, and the coke may be removed from the catalyst (i.e., regenerating the catalyst) by a combustion reaction. For example, oxidizer (such as air) may be fed into the combustor 350 via the air inlet 428. Alternatively or additionally, such as when coke is not formed on the catalyst, a supplemental fuel may be injected into the combustor 350, which may be burned to heat the catalyst. Following combustion, the processed catalyst may be separated in the catalyst separation section 310 and delivered back into the reactor portion 200 via standpipe 424.

EXAMPLES

The following examples are illustrative in nature and should not serve to limit the scope of the present application.

A model was constructed to calculate expected suspension density, conversion, and superficial gas velocity in a fluidized bed reactor as a function of reactor geometry. The fluidized bed reactors had geometry similar to that of FIG. 1 or FIG. 2, but with specified tapering of the main reactor vessel. Specifically, the suspension density, conversion, and superficial gas velocity were calculated as a function of height for varying reactor geometries with outwardly tapering walls. Calculations for hydrodynamics were based on the methods disclosed in Kunii, D., and Levenspiel, O., Entrainment of solids from fluidized beds, *Powder Technology*, 61, 1990, 193-206. The model simulated a reaction where two molecules of product gas was formed per each molecule of reactant gas. The gas velocity at the bottom of the reactor was 3.5 ft/s.

Figure 4A:
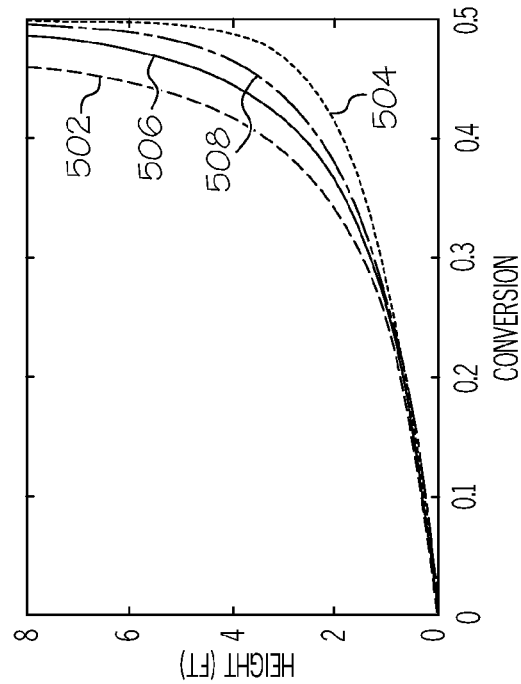
FIGS. 4A-4D depict modeled data of three example embodiments and a comparative example, according to one or more embodiments described herein.
Figure 4B:
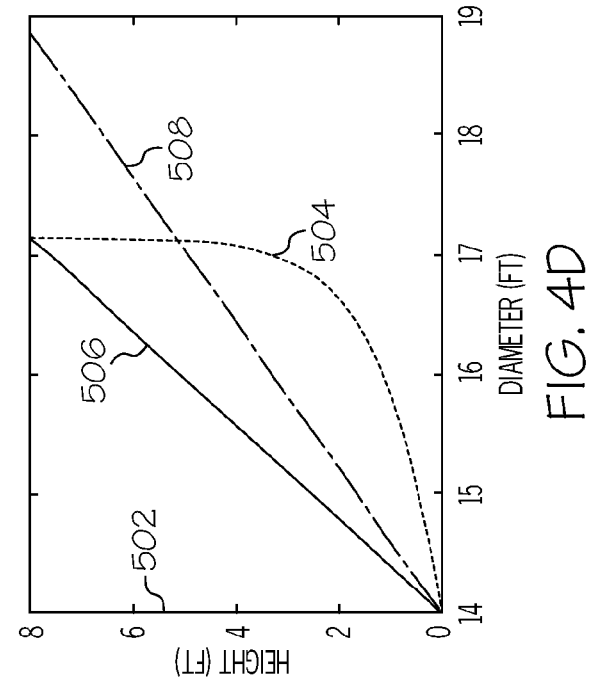
Figure 4C:
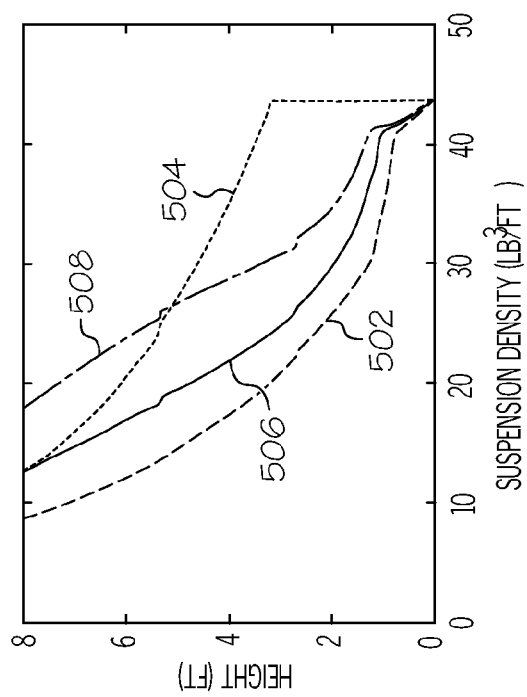
Figure 4D:
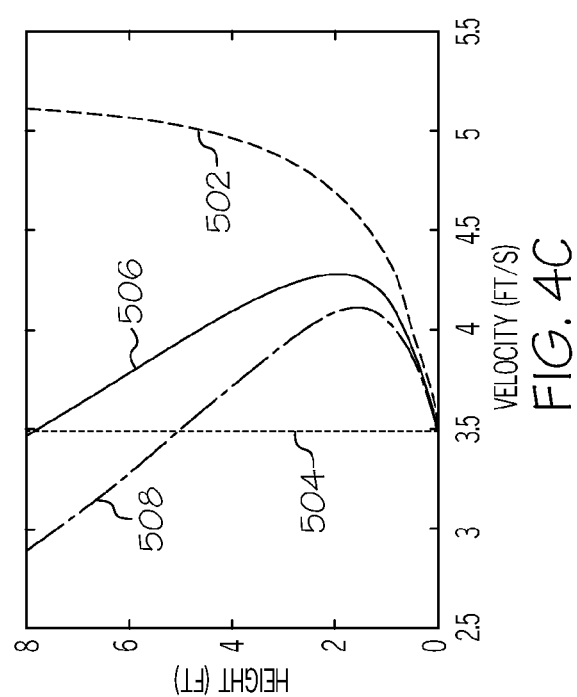

In a first tested embodiment (a comparative example), a constant reactor diameter was tested. Lines 502 in FIGS. 4A, 4B, and 4C depict the suspension density, conversion, and superficial gas velocity respectively as a function of height of the reactor. FIG. 4D depicts in line 502 the constant diameter of the main reactor vessel. The results shown that with constant diameter, the suspension density was significantly reduced at increased heights while the superficial gas velocity was significantly increased at increasing heights.

A second tested embodiment is depicted as line 504 in FIGS. 4A, 4B, 4C, and 4D. In this embodiment, the geometry of the main reactor vessel allows for constant superficial gas velocity as a function of reactor height. In such a configuration, suspension density remains greater at all heights as compared to the constant diameter comparative example. The geometric profile of the main reactor vessel can be seen in FIG. 4D for such an embodiment, where slope of the profile increases with increasing height, and the upper half of the main reactor vessel is nearly cylindrical.

A third tested embodiment is depicted as line 506 in FIGS. 4A, 4B, 4C, and 4D. In this embodiment, the geometry of the main reactor vessel is linear, where the diameter at the downstream portion of the main reactor vessel is equal to that of the second tested embodiment. In such a configuration, suspension density and superficial gas velocity are both more desirable than in the comparative example.

A fourth tested embodiment is depicted as line 508 in FIGS. 4A, 4B, 4C, and 4D. In this embodiment, the geometry of the main reactor vessel was linear like the third example embodiment, but was wider at the downstream portion so that conversion of 0.5 could be achieved. This embodiment also increased suspension density and reduced superficial gas velocity as compared with the comparative example.

The residence time and average density for the first, second, third, and fourth example embodiments was calculated, and is depicted in Table 1, below.

TABLE 1

| Example | Residence Time | Average Density |
|---|---|---|
| 1 | 1.68 | 12.1 |
| 2 | 2.03 | 12.0 |
| 3 | 2.29 | 14.1 |
| 4 | 2.24 | 13.3 |

As shown in FIG. 4B, the reactor designs with tapered geometry have higher conversion at lower heights. Therefore, it is contemplated that the tapered geometric designs disclosed herein may be utilized to build and operate reactors which are shorter than conventional reactors (relative to overall feed rate). Additionally, without being bound by theory, it is believed that the shorter reactor may result in a reduced residence time, which may result in higher selectivity for dehydrogenation reactions due to reduced thermal cracking reactions.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for converting a reactant gas, the method comprising:
   introducing the reactant gas to a fluidized bed reactor such that the reactant gas is contacted by a catalyst, wherein the fluidized bed reactor comprises a main reactor vessel comprising an upstream portion and a downstream portion, and a transition section connected to the downstream portion of the main reactor vessel, and wherein the reactant gas enters the fluidized bed reactor at or near the upstream portion of the main reactor vessel, and wherein the transition section projects inwardly from the main reactor vessel to a riser;
   catalytically reacting the reactant gas to form a reaction product in the fluidized bed reactor, wherein the reaction results in additional gas molecules relative to the reactant gas; and
   passing the reaction product and any unreacted reactant gas through the transition section and into the riser, wherein the riser is connected to the transition section;
   wherein the main reactor vessel is tapered such that the upstream portion of the main reactor vessel comprises a lesser cross-sectional area than the downstream portion of the main reactor vessel.

2. The method of claim 1, wherein a superficial velocity of the gases in the fluidized bed reactor at the downstream portion of the main reactor vessel is less than or equal to 140% of a superficial velocity of the gases in the fluidized bed reactor at the upstream portion of the main reactor vessel.

3. The method of claim 1, wherein a suspension density in the fluidized bed reactor at the downstream portion of the main reactor vessel is greater than or equal to 25% of a suspension density of the gases in the fluidized bed reactor at the upstream portion of the main reactor vessel.

4. The method of claim 1, wherein the reaction product is a dehydrogenation product of the reactant gas.

5. The method of claim 4, wherein the reactant gas comprises one or more of ethane, propane, n-butane, isobutane, and ethylbenzene.

6. The method of claim 1, wherein the main reactor vessel comprises a central portion between the downstream portion and the upstream portion, and wherein a superficial velocity of the gases in the fluidized bed reactor at the central portion of the main reactor vessel is from 60% to 140% of a superficial velocity of the gases in the fluidized bed reactor at the upstream portion of the main reactor vessel.

7. The method of claim 1, wherein the main reactor vessel comprises a central portion between the downstream portion and the upstream portion, and wherein a superficial velocity of the gases in the fluidized bed reactor at the central portion of the main reactor vessel is from 80% to 120% of a superficial velocity of the gases in the fluidized bed reactor at the upstream portion of the main reactor vessel.

8. The method of claim 1, wherein a superficial velocity of the gases in the fluidized bed reactor at the downstream portion of the main reactor vessel is from 80% to 120% of a superficial velocity of the gases in the fluidized bed reactor at the upstream portion of the main reactor vessel.

9. The method of claim 1, wherein the main reactor vessel comprises a slope that is substantially constant.

10. The method of claim 1, wherein the main reactor vessel comprises a slope that is less at or near the downstream portion than at or near the upstream portion.

11. The method of claim 1, wherein the main reactor vessel comprises a central portion between the downstream portion and the upstream portion, and wherein a cross-sectional area of the central portion is less than the cross-sectional area of the downstream portion and greater than the cross-sectional area of the upstream portion.

12. A method for converting a reactant gas, the method comprising:
   introducing the reactant gas to a fluidized bed reactor such that the reactant gas is contacted by a catalyst, wherein the fluidized bed reactor comprises a main reactor vessel comprising an upstream portion and a downstream portion, and a transition section connected to the downstream portion of the main reactor vessel, and wherein the reactant gas enters the fluidized bed reactor at or near the upstream portion of the main reactor vessel, and wherein the transition section projects inwardly from the main reactor vessel to a riser;

catalytically reacting the reactant gas to form a reaction product in the fluidized bed reactor, wherein the reaction results in additional gas molecules relative to the reactant gas; and passing the reaction product and any unreacted reactant gas through the transition section and into the riser, wherein the riser is connected to the transition section;

wherein the main reactor vessel is tapered such that the upstream portion of the main reactor vessel comprises a lesser cross-sectional area than the downstream portion of the main reactor vessel such that a superficial velocity of the gases in the fluidized bed reactor at the downstream portion of the main reactor vessel is less than or equal to 140% of a superficial velocity of the gases in the fluidized bed reactor at the upstream portion of the main reactor vessel, or a suspension density in the fluidized bed reactor at the downstream portion of the main reactor vessel is greater than or equal to 25% of a suspension density of the gases in the fluidized bed reactor at the upstream portion of the main reactor vessel, or both.

13. The method of claim 12, wherein the reaction product is a dehydrogenation product of the reactant gas.

14. The method of claim 13, wherein the reactant gas comprises one or more of ethane, propane, n-butane, isobutane, and ethylbenzene.

* * * * *